United States Patent
Gehring

(10) Patent No.: US 8,230,724 B2
(45) Date of Patent: Jul. 31, 2012

(54) MEASUREMENT CHAMBER AND RESONATOR

(75) Inventor: Frank K. Gehring, Buhlstrasse (DE)

(73) Assignee: Andreas Hettich GmbH & Co. KG, Tuttlingen (DE)

( * ) Notice: Subject to any disclaimer, the term of this patent is extended or adjusted under 35 U.S.C. 154(b) by 767 days.

(21) Appl. No.: 12/294,959

(22) PCT Filed: Mar. 28, 2007

(86) PCT No.: PCT/EP2007/002729
§ 371 (c)(1),
(2), (4) Date: Jan. 2, 2009

(87) PCT Pub. No.: WO2007/112897
PCT Pub. Date: Oct. 11, 2007

(65) Prior Publication Data
US 2009/0173158 A1    Jul. 9, 2009

(30) Foreign Application Priority Data
Mar. 31, 2006 (DE) .................... 10 2006 015 512

(51) Int. Cl.
G01H 13/00 (2006.01)
G01N 29/036 (2006.01)

(52) U.S. Cl. ............... 73/61.49; 73/61.79; 73/64.53; 73/579

(58) Field of Classification Search ........... 73/61.45, 73/61.49, 61.75, 61.79, 64.53, 579, 24.01, 73/24.03, 24.06
See application file for complete search history.

(56) References Cited

U.S. PATENT DOCUMENTS

| | | | |
|---|---|---|---|
| 3,653,253 A | * | 4/1972 | Olin .................. 73/24.03 |
| 6,189,367 B1 | * | 2/2001 | Smith et al. ......... 73/19.03 |
| 2007/0145862 A1 | | 6/2007 | Kimura et al. |

FOREIGN PATENT DOCUMENTS

| | | | |
|---|---|---|---|
| JP | 3-279840 | * | 12/1991 |
| JP | 3-295443 | * | 12/1991 |
| WO | WO 02/12873 | | 2/2002 |
| WO | WO 02/47246 | * | 6/2002 |
| WO | WO 2004/001392 | * | 12/2003 |
| WO | WO 2005/066621 | | 7/2005 |
| WO | WO 2006/070940 | * | 7/2006 |

OTHER PUBLICATIONS

Comparison of Surface Transverse Wave (STW) and Shear Horizontal Acoustic Plate Mode (SHAPM) Devices for Biochemical Sensors, 1997 IEEE International Frequency Control Symposium, Michael G. Schweyer et al., pp. 147-155, 1997.

Microparticle Concentration in Short Path Length Ultrasonic Resonators: Roles of Radiation Pressure and Acoustic Streaming, Larissa A. Kuznetsova, pp. 1956-1966 J. Accoust. Soc. Am. 116 (40, PT. 1, Oct. 2004.

* cited by examiner

*Primary Examiner* — Daniel Larkin
(74) *Attorney, Agent, or Firm* — Woodling, Krost and Rust

(57) ABSTRACT

The invention relates to an apparatus comprising a measurement chamber and a resonator, which can be integrated in the measurement chamber via a quick-action closure, for the liquid sensor system and for verification and measurement of the concentration of materials, substances, particles and/or microorganisms in liquids. The invention is characterized in that the resonator is held only on its outer circumference by a thin elastomer ring, and in that at the radial distance of the external diameter of the resonator, the elastomer ring on the one hand rests on an upper sealing ring of the measurement chamber, forming a seal, and on the other hand rests on a holding ring.

41 Claims, 6 Drawing Sheets

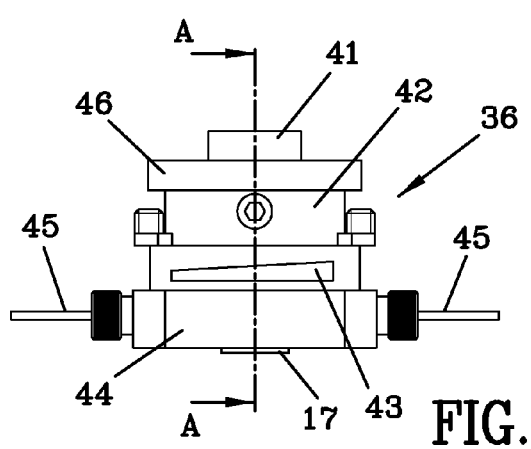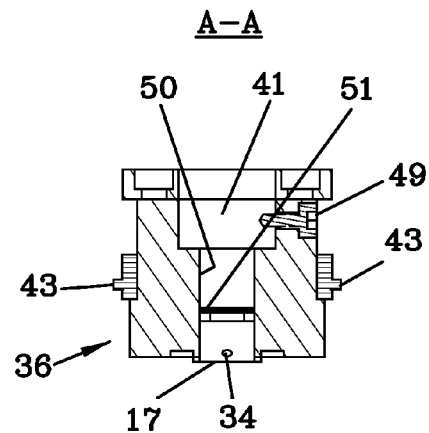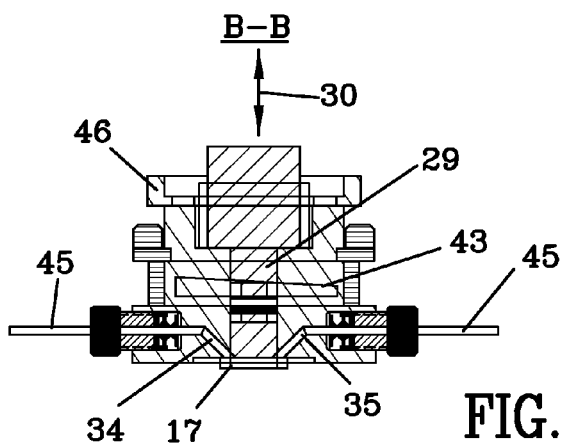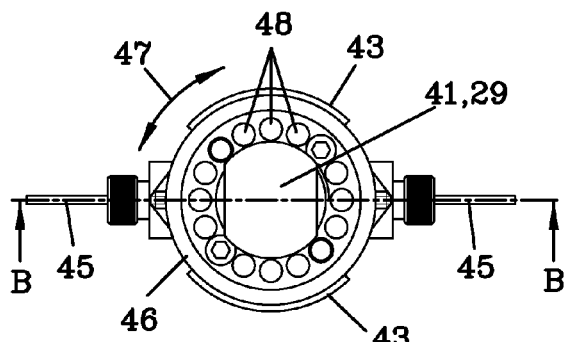
FIG. 7
FIG. 10
FIG. 8
FIG. 9

MEASUREMENT CHAMBER AND RESONATOR

This application claims priority to German Patent Application DE 10 2006 015 512.2 filed Mar. 31, 2006.

FIELD OF THE INVENTION

The invention pertains to a device consisting of a measurement chamber and a resonator.

BACKGROUND OF THE INVENTION

The object of DE 40 13 665 A1 is a sensor for the detection of a substance in a liquid. The sensor is designed as a resonator, which is integrated into a measurement chamber by means of a sealing device.

One of the end surfaces of this resonator is in contact with the liquid to be tested. The substance in question, the presence of which is to be detected or the concentration of which is to be measured, accumulates on this end surface and thus leads to a change in the resonance frequency and/or in the vibration amplitude of the resonator. Differences in the properties of the liquid can also cause changes in these two measurement variables.

The invention therefore pertains in particular to the area of piezoelectric quartz oscillator sensors which are used to detect the presence and/or to measure the concentration of biological, chemical, or biochemical substances and of microorganisms in liquids or to determine the properties of a liquid.

With respect to the further functions of a resonator of this type, reference is made to the disclosure content of DE 40 13 665 A1, the entire content of which is to be considered part of the disclosure content of the present invention.

A similar state of the art can be derived from DE 197 34 706 A1, which also describes a piezoelectric resonator, which is integrated into a measurement chamber by means of a sealing arrangement and which is also used to examine biological, chemical, or biochemical substances.

For quartz oscillators operating in the gas phase, quartz oscillator mounts are usually used in which the quartz oscillator is contacted and held in place by two electrical lead wires with bow-like ends. The lead wires pass through an electrically isolated base plate, onto which an electromagnetic shield can be placed. A different type of method for mounting and contacting the oscillator can be found in DE 34 46 612 and DE 199 26 944.

In the known mounting system for piezoelectric quartz oscillators operating in the liquid phase, the upper end surface of the resonator is sealed either by the use of a sealing element, usually a silicone ring, which is pressed onto the upper end surface of the quartz oscillator, or by the use of an adhesive to glue the quartz oscillator into a holder (DE 197 34 706 A1). Contact springs, bond wires, conductive rubber, or conductive adhesive elements are used to establish the necessary electrical contact (DE 401 13 665). In DE 197 34 706 A1, the quartz oscillator is integrated permanently into the measurement chamber, which consists of an injection-molded part, by an adhesive. Electrical contact is accomplished here by bond wires and thus without mechanical tension. This measurement chamber, which is also called a "flow-through cell", can be installed in, and removed from, the measurement system without affecting the parameters of the quartz oscillator.

In the case of the mounting principles of DE 401 13 665 A1, according to which a sealing ring is pressed onto the upper end surface, it is often true that the surface of the quartz oscillator can be readily accessed for applying a biological coating and that in principle the surface of the quartz oscillator is also optically accessible after it has been installed in the measurement chamber. The use of this sealing principle, however, means that, when the quartz oscillator is removed, it will be subjected to a different degree of mechanical tension when it is reinstalled. This means that the resonator cannot be removed and quickly reinstalled during a measurement to allow the surface of the quartz oscillator to be characterized under a light microscope, a scanning force microscope, etc.

Maintaining uniform electrical contact under this principle is also very difficult or perhaps even impossible. In addition, the process of integrating the quartz oscillator into the measurement chamber or into the measurement system so that the proper contact is achieved is very time-consuming and can be accomplished only by skilled technical personnel.

Not infrequently the pressing of the seal onto the quartz oscillator leads to such strong mechanical stress that the quartz oscillator breaks during installation.

Another disadvantage of this method is that the wetting area of the upper surface of the quartz oscillator is not precisely defined. If the seal is not pressed on firmly enough, wetting liquid escapes, which can cause the two quartz electrodes to become short-circuited. If the quartz oscillator is installed and/or removed with tweezers, for example, it is again possible for the quartz oscillator to be broken, and in cases where a biological coating is present, this coating can be at least partially scraped off or destroyed. A very crucial disadvantage of this mounting principle with respect to the analysis of liquids which contain, for example, "heavy" particles or human cells is the flow barrier necessarily caused by a large seal or a large sealing ring. It is therefore possible only under certain limited conditions to introduce the liquid tangentially, and after a measurement the analyte can be removed, if at all, only by the use of very high flow rates. Such high flow rates affect in turn the oscillation behavior of the quartz oscillator and demand a very tight seal even at high pressures.

In the case of the mounting system described in DE 197 34 706A1, in which the quartz oscillator is integrated permanently into the measurement chamber by an adhesive, it is not possible to characterize the surface of the quartz oscillator by other methods (light microscopy, scanning force microscopy, etc.), nor is it possible to provide a biological coating or to clean the surface of the quartz oscillator outside the measurement chamber. In the case of other mounting principles, according to which the quartz oscillator is glued into a mount, the quartz oscillator can be removed from the measurement chamber as in the case of the "clamping" method, and its surface is therefore often accessible for the application of a biological coating, and in principle it is also usually optically accessible in the installed state.

The systems just mentioned, however, suffer from the disadvantage that the gluing process can subject the quartz oscillator to mechanical stress. Another disadvantage is the laborious nature of the task of gluing the quartz oscillator into the mounting system, which demands that the adhesive be metered and positioned with great accuracy. Residues of adhesive, which result from the imprecise application of the adhesive or from the deposition of adhesive vapors on areas near the center of the oscillator surface, change the oscillation characteristics and often make it impossible to apply a biological coating. Adhesives, such as silicone adhesives, which have the advantage of still having good elasticity values even in the cured state and which are almost completely biocompatible, suffer from the disadvantage of a relatively long curing time. Fast-curing adhesives such as those based on cyanoacrylate have very low elasticity values and as they cure can therefore subject quartz oscillators to severe stress.

A leak-tight seal can be achieved with these adhesives only if the gaps between the mount and the quartz oscillator are very small. This makes assembly extremely difficult. In addition, these adhesives, which have only limited biocompatibility, readily evaporate, and the vapors therefore can easily settle on areas near the center of the resonator.

It is usually quite complicated to produce the necessary electrical contacts in these mounting systems, i.e., the systems in which the quartz resonator is glued in place, because it must be done either simultaneously with the application of the adhesive, or, in the case of the mounts which can be removed from the measurement chamber, by the use of elastic contact pins or the like, which are pressed against the end surface operating in the gas phase.

When contact pins are used to establish electrical contact, the quartz oscillator is again subjected to mechanical stress. When the quartz oscillator is glued in place, there will always be slight differences in positioning between one oscillator and another. This mechanical stress will therefore also be different after the removal and reinstallation of an individual resonator, which makes it difficult to characterize the surface of the oscillator by other methods during a measurement.

As a result of the slight differences in the positioning of the quartz oscillator, the forces which the contact pins exert on the oscillator can also become so strong that the oscillator will break or that the adhesive seal will be loosened and leaks will develop. This problem is often prevented by providing a ring-shaped stop lip, but as a result it becomes difficult if not impossible to introduce a tangential flow in the case of these mounting systems. Because of the disadvantages mentioned above, therefore, it is very difficult to use an adhesive to install quartz oscillators in oscillator mounts in an automated and/or low-cost manner.

SUMMARY OF THE INVENTION

The invention is therefore based on the task of mounting a resonator in a measurement chamber in such a way that it is subject to little or no damping and no leaks can develop. In addition, tangential flow should be possible, so that the biological layer will not be washed off and the influence of the flow parameters on the measurement accuracy will be reduced.

The essential feature of the invention is that the resonator is mounted and sealed only around its outer circumference by a thin elastomeric ring, and that, a certain radial distance away from the outside diameter of the resonator, one side of the film ring rests with a sealing action against an upper sealing ring of the measurement chamber, whereas the other side rests on a support ring.

The technical teaching indicated above offers the advantage that now the sealing surfaces for the seal between the measurement chamber and the measurement device containing the resonator are no longer positioned in the area of the resonator but rather are located radially outward, a certain distance away from the outside circumference of the resonator. Thus there is no longer any need for the sealing surfaces themselves to be formed on the resonator, a situation which is associated with severe disadvantages, as described above in conjunction with the state of the art.

The essence of the invention therefore lies in the fact that the resonator is mounted and sealed only by a very thin elastomeric ring extending around its outside circumference and that, a certain radial distance away from the mounting, the elastomeric ring, which rests only on the outer part of the resonator, is mounted between two cooperating surfaces, one of these surfaces being designed as a sealing ring. The term "elastomeric ring" for the mounting of a disk-shaped resonator is to be understood in a very broad sense according to the present invention.

In a first preferred embodiment, this elastomeric ring consists merely of a film ring, which has the thickness of conventional film material, namely, a thickness in the range of 50-300 µm, and consists of conventional film material such as PVC or the like. It is preferred here for this film ring to be as thin as possible and to be coated with a layer of adhesive on one side, because then the resonator can be mounted in the ring by way of this adhesive layer, which will contact only the outside circumference of the resonator.

In addition to an adhesive mounting between the film ring and the resonator, however, there are also other mounting principles which are being claimed as essential to the invention. Accordingly, as another, detachable type of mounting, for example, an arrangement can be provided in which the film ring forms an upper and a lower circumferential annular groove, and the outside circumference of the disk-shaped resonator is pushed into this circumferential annular groove.

Instead of a circumferential mounting of the disk-shaped resonator in a circumferential groove, it is also obviously claimed that the resonator can be mounted only at certain separate points by individual retaining ribs distributed around the circumference.

Instead of an adhesive seal and instead of a sealed mounting in an annular groove, it is also claimed as an elaboration of the invention that a nonadhesive film is simply laid under an applied pressure on the edge area of the resonator, and that the necessary sealing action is achieved only by the applied pressure, not by an adhesive bond.

The term "disk-shaped" resonator refers only to a preferred exemplary embodiment of the invention. It is also obviously claimed as essential to the invention that the resonator could have different outlines. For example, it could be rectangular, square, or hexagonal or be designed as a parallelogram or the like. The use of the term "disk-shaped" resonator is therefore intended only as a way if simplifying the explanation of a preferred exemplary embodiment.

Accordingly, the sealing arrangement, which is described in greater detail below, must obviously be adapted to the actual outline of the resonator. The important point in all of the exemplary embodiments is in any case that the sealing arrangement extends only a very short distance over the outer part of the resonator, i.e., over the part where its active, oscillating area is, and that as a result the resonator is supported without any impairment to its behavior.

In addition to the previously mentioned adhesive mounting or the mounting by insertion into a groove, it is obviously also possible for the film ring to be electrostatic and for the outer area of the resonator to be attached to this film ring by electrostatic attraction.

In this connection it is therefore also possible for the elastomeric ring to consist not of a plastic film but rather of a metal foil or of plastic-and-metal or plastic-and-ceramic composite material, all of which are to be included under the inventive idea of the present invention.

The important point is that, to improve the oscillatory behavior of the resonator, the resonator is sealed without tension only in its outer area, where the amplitude of the oscillations is very small. The second sealing surface, furthermore, is shifted radially outward from the outside circumference of the resonator into the area of the measurement chamber. As a result, the resonator is mounted in such a way that its oscillations are damped as little as possible, and it is subject to the minimum possible amount of tension underneath or in the previously mentioned elastomeric ring (film ring).

Instead of attaching a separate mounting (ring-shaped piece of film) to the resonator to hold it in place, it is also possible to coat the resonator itself with the film material or to deposit the material by sputtering.

This means that, for example, a layer of gold can be deposited from the vapor phase onto the surface of the resonator. This gold layer would be extended radially outward beyond the outside circumference of the resonator to form the elastic ring. The ring could also be formed by a plastic coating or by other materials.

Another important point of this exemplary embodiment is that the ring is deposited by sputtering directly onto the surface of the resonator, so that an absolutely flat transition— without the intermediate presence of any shoulders of plastic material—is present in the measurement chamber. The measurement chamber is therefore completely flat and has no projecting edges. Not even the smallest shoulder-like transition is present, as is the case in the exemplary embodiment to be described later, where the film ring has a thickness of, for example, 100 μm, and where its disk-like inside circumference extends partially over the outside circumference of the resonator and holds it in place there.

If it is also desired to inject "heavy" particles, for example, or human cells, the mounting system should interfere only slightly if at all with the flow of liquid. Otherwise, any flow barriers which may be present will cause the "heavy" particles or cells to settle in the measurement chamber, from which they can no longer be removed. If the surface of the resonator operating in the liquid phase has been provided with a biological coating, the mounting system should be designed in such a way that the flow can be introduced tangentially, so that the biological layer will not be "washed away" and so that, at the same time, variations in the flow parameters will have less of an influence. Visual accessibility is also crucial so that, after the quartz oscillator has been mounted in the measurement chamber, its surface can be observed while the measurement chamber is being filled and the analyte is accumulating on it. Another important point is the accessibility of the surface of the quartz oscillator so that it can be provided with one or more biological layers after the oscillator installed in the mounting system has been removed from the measurement chamber. This accessibility, together with the ability to remove the quartz oscillator installed in its oscillator mount from the measurement chamber and to reinstall it again quickly without influencing the parameters of the oscillator, opens up the possibility of characterizing the surface of the oscillator during a measurement, e.g., by the use of a light microscope, a scanning force microscope, etc. The quartz oscillator mount should also make it much easier to handle the oscillator outside the measurement chamber. This is especially true for oscillators which have been provided with a biological layer for the purpose of biosensing. The direct handling of the quartz oscillator with tweezers can lead very quickly to the cracking of the fragile quartz. Touching the surface of the quartz with tweezers also destroys the biological layer.

The inventive measures result in the following advantages:
- complete sealing of the upper end surface (prevention of an electrical short-circuit between the upper and lower electrodes);
- faster removal of the quartz oscillator installed in its oscillator mount from the measurement arrangement and faster reinstallation (integration into the measurement chamber or the flow system; electrical contact for exciting the oscillations and for tapping the sensor signal);
- a defined wetted surface area of the quartz oscillator (problem: change in the signal as the result of a change in the wetted surface area);
- low damping and mechanical stress caused by the sealing of the quartz oscillator;
- no influence on the parameters of the quartz oscillator by removal and re-installation into the measurement chamber or the flow system (uniform electrical conditions, uniform mechanical stresses on the quartz oscillator, and uniform damping);
- less contact resistance between the quartz oscillator and the mounting;
- the most complete possible removal of all particles and cells from the measurement chamber after the measurement has been completed (cleaning);
- variable cell volumes possible (no dead space);
- the surface of the quartz oscillator is visually accessible in principle after it has been installed in the measurement chamber;
- easy removal and reinstallation of the quartz into the measurement chamber without damage to any biological coating which may be present;
- easy handling of the fragile quartz outside the measurement arrangement (biological coating, regeneration, observation under the microscope, etc.);
- possibility of tangential flow introduction (relative to the surface of the quartz oscillator) into the measurement chamber=less influence on variation of the flow parameters, no "rinsing-off" of the biological layer;
- uniform distribution of the analyte over the surface of the quartz oscillator (differences in radial sensitivity);
- possibility of biological or chemical coating of a quartz resonator surface in and outside the measurement chamber (quartz oscillator mounting made of biocompatible materials, especially adhesives, which are as inert as possible and thus allow no deposition of nonspecific chemical and biological substances).

In contrast to the known mounting systems described above, the invention described here provides a film ring, which is coated with adhesive, has a larger outside diameter than the quartz oscillator, and is applied to the edge of the surface of the quartz oscillator to be wetted and thus seals the upper end surface.

The inside diameter of the film ring is selected so that only the outer area of the upper end surface of the quartz oscillator, where the amplitude of the oscillations is very small, is covered by the film. The part of the film ring projecting beyond the quartz oscillator is bonded to a plastic ring (mounting ring). The adhesive is cured by heating the film briefly with a soldering iron, for example, or with a heating plate.

Between the quartz oscillator and the plastic ring surrounding it there is a gap, which is wide enough to ensure that the quartz oscillator, although held by the film, is held in the mounting so that it is essentially free-floating. Because the film has a relatively high coefficient of linear expansion, furthermore, the oscillator is not under any mechanical stress as a result of the mounting process.

After the oscillator has been installed in its mounting, the necessary electrical contact is established on the lower end surface of the quartz oscillator by laying it on a second plastic ring, the so-called "contact ring", to the surface of which two metal electrodes have been attached.

The outside diameter of the contact ring is smaller than the inside diameter of the support ring, and its height is lower than that of the support ring by an amount equal to the thickness of the oscillator. As a result, the contact pads on the lower end surface are positioned precisely above the electrodes of the contact ring.

When a force is exerted on the support ring and on the outer part of the contact ring by way of, for example, a sealing ring of a specially designed measurement chamber, the quartz oscillator is pressed in a precisely defined manner onto the contact ring as a result of the elastic properties of the film, and very good electrical contact is established without any mechanical stress on the quartz oscillator.

The inside diameter of the contact ring is selected so that only the edge areas of the lower end surface of the resonator, which oscillate at very low amplitude, rest on it. The shear oscillations of the quartz oscillator are therefore damped by the contact ring to only a small degree.

In a corresponding design of the measurement chamber belonging to the invention, it is possible as a result of the mounting system described above for the measurement chamber to be pressed down from above the quartz resonator by a quick-release fastening, e.g., a bayonet fastener, to form a liquid-tight seal without causing any significant mechanical stress on the quartz oscillator and without subjecting it to a different degree of mechanical stress each time the oscillator is removed and re-installed. Because the film is very thin, i.e., <0.1 mm, and therefore does not represent a significant barrier to the flow of liquid, the flow can be introduced tangentially, provided that the geometry of the measurement chamber has been selected appropriately. This mounting system makes it possible for the fluid feed lines to be placed outside the optical window, which makes it possible in turn for the first time to observe the surface of the quartz oscillator during a measurement or during the injection of a liquid, etc., while the flow is being introduced tangentially at the same time. In addition, this arrangement makes it possible to use an adjusting screw to adjust precisely the height of the optically transparent plunger and thus the volume of the measurement chamber to different values. Thermostatic control by means of a Peltier system, for example, can be provided from underneath without interfering with visual access.

During the measurement, the surface of the quartz oscillator is visually accessible in spite of the tangential introduction of the flow. As a result, it is possible to observe the accumulation of the analyte on the surface of the quartz oscillator, the inclusion of air bubbles, and the filling process. In addition to the scientific advantages, this visual accessibility also makes it possible to monitor the process during automated measurements.

As a result of the quartz oscillator mounting principle described above, it is possible to seal the upper end surface of the oscillator reliably. In addition, the wetted surface area remains precisely defined even after removal and re-installation of the oscillator, and, in contrast to the prior systems, no flow barriers are present even when the flow is introduced tangentially. As a result, even "heavy" particles or "large" human cells can be removed from the measurement chamber after a measurement. This is what makes it possible for analyses of whole human blood, for example, to be made in this way for the first time.

The volume of the measurement chamber can be adjusted. Biocompatibility is guaranteed.

Easy handling of the quartz oscillator outside the measurement chamber. (The surface of the oscillator is very readily accessible for the application of biological coatings. Once the oscillator has been installed in the oscillator mount, tweezers can be used to manipulate it by gripping the outer support ring. It is thus possible to remove and to reinstall the oscillator without destroying it as a result of excessive mechanical stress and without destroying the biological coating.)

The measurement chamber can be attached and the necessary electrical contact established simultaneously with the help of a quick-release fastener without influencing the parameters of the oscillator. This is the precondition for rapid access to the oscillator during a measurement and thus for the characterization of the surface of the resonator by other methods (light microscopy, scanning force microscopy, etc.) in order to verify intermediate results. Because the quick-release fastener makes it so easy to install the quartz oscillator in the measurement chamber, highly trained personnel are not required to do it, and it is even conceivable that, because it is so simple, the process of attaching the measurement chamber could be automated.

The object of the present invention can be derived not only from the objects of the individual claims but also from the combination of the individual claims with each other.

All of the information and features disclosed in the documents, including the abstract, and especially in the three-dimensional designs shown in the drawings, are claimed as essential to the invention insofar as they are novel with respect to the state of the art either individually or in combination.

In the following, the invention is described on the basis of drawings, which illustrate only one possible embodiment. Additional features essential to the invention and advantages of the invention can be derived from the drawings and from the description of them.

BRIEF DESCRIPTION OF THE DRAWINGS

FIG. 7 shows a side view of the measurement chamber;

FIG. 8 shows a cross section through the measurement chamber along line BB of FIG. 9;

FIG. 9 shows a top view of the measurement chamber;

FIG. 10 shows a cross section along line A-A of FIG. 7;

DESCRIPTION OF THE INVENTION

Figure 1:
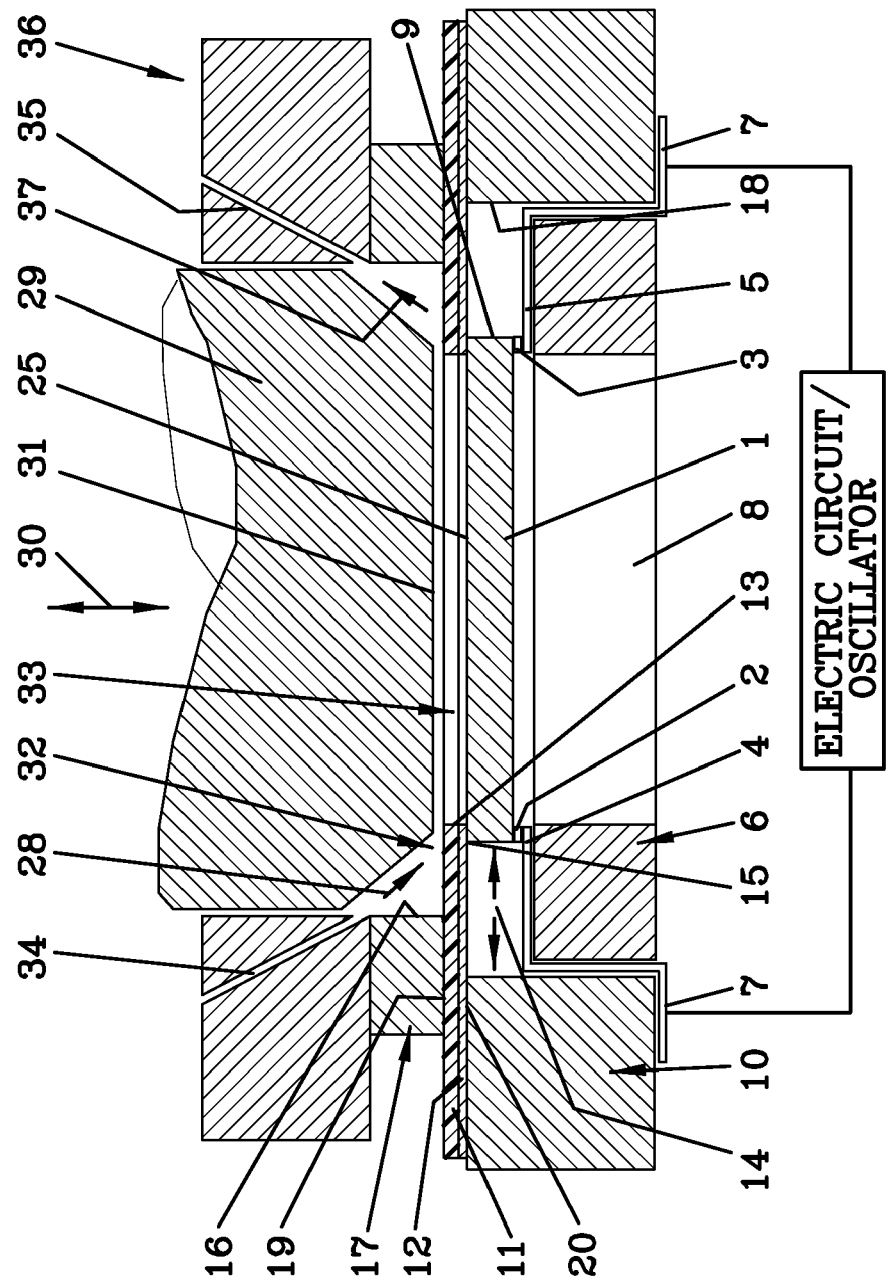
FIG. 1 shows a cross section through a measurement chamber according to one exemplary embodiment of the invention.

FIG. 1 shows an enlarged, schematic view of the lower part of a measurement chamber 36 according to FIGS. 7-11 and a measuring device, which is connected and sealed to the lower part of the measurement chamber 36.

The design of the measuring device is described in the following.

A disk-shaped resonator 1 (e.g., with the size of a 1-cent piece), serving as a disk-shaped oscillator, is supported in an inventive mounting.

At opposite points on its outside circumference, the resonator has two opposing contact surfaces 2, 3, which are very thin and which, in the exemplary embodiment according to FIG. 1, are shown with exaggerated thickness.

In reality, these contact surfaces 2, 3 are connected to the bottom surface of the resonator 1 in such a way that they are essentially flush with it.

The contact surfaces 2,3 of the resonator 1 rest with a precisely defined contact pressure on the opposing contact surfaces 4, 5 of a contact ring 6.

The contact ring 6 is preferably made of an electrically insulating material, and the contact surfaces 4, 5 are designed merely as conductive silver tracks or the like.

Contact surfaces 4, 5, which are arranged opposite each other and are electrically insulated from each other, are therefore present on the contact ring 6 and are connected in an electrically conductive manner to the contact surfaces 2, 3 of the resonator 1.

The current leads of these contact surfaces 4, 5 are connected to the output of an oscillator circuit; the electrical oscillation frequency of the oscillator circuit tracks the mechanical oscillation of the resonator.

Of course, the connection to an oscillator circuit explained above is to be understood merely as an example. It is obvious that other measuring devices can also be used, such as a device for measuring impedance or a signal generator, which transmits a precisely defined signal to the resonator 1 to excite it.

The resonator 1 is therefore suspended completely freely above a cavity 8, which is formed in the interior of the disk-shaped contact ring 6.

It is important now to mention that an adhesive film is bonded to the outside diameter 9 of the resonator 1, this film being formed as a film ring 11 in the exemplary embodiment shown here. The outer periphery of the surface 25 of the resonator engages film ring 11.

The film ring 11 together with its adhesive coating is shown in highly exaggerated form in FIG. 1 and in the following figures so that the size relationships can be understood more clearly.

In reality, the film ring is much thinner than the resonator. If we assume that the resonator has, for example, a thickness of 0.2 mm and that its oscillation frequency is 10 MHz, the thickness of the film will be in the range of 50-200 μm.

Of course, other thicknesses, including greater thicknesses, are also possible, because the core idea of the invention is that the resonator 1 is mounted in the attachment area between its outside diameter 9 and the associated inside diameter of the film ring 11 in such a way that the oscillator is damped as little as possible and is supported without any mechanical stress.

Instead of the film ring shown here with a lower adhesive surface 12, it is also possible to use rings which have been produced by casting, drawing, or injection-molding. The important point, however, is that the film ring 11 or ring of equivalent material shows elastomeric behavior.

It is essential to the mounting system according to the invention not only that the oscillator is damped as little as possible by the film ring but also that it is held in place accurately at all times, is free of tension at all times, and is independent of outside influences, especially those which would be exerted by a sealing arrangement with the rings 17 and 10 as described below.

The important point here is that the film ring 11 extends radially outward beyond the outside diameter 9 of the resonator; this results in an open gap 14, which means that the resonator 1 is practically free-floating.

The inside diameter 13 of the film ring extends over the outside diameter of the resonator 1 by only a small amount such as 0.2 mm, which therefore ensures that the oscillating parts of the resonator 1 are not affected by the mounting.

It also important that, a certain distance radially outward from the outside diameter of the resonator 1, the film ring 11 is held between two opposing surfaces, one of these surfaces serving as a sealing site. The sealing site is formed by a ring-like, circumferential sealing ring 17, located under the bottom surface of the measurement chamber 36, whereas the opposite surface is formed by a support ring 10, which consists of a dimensionally stable material such as polypropylene, PPE, or the like. This support ring 10 forms the opposing surface for the upper, opposite sealing ring 17, and its design can be modified over a wide range. It can even be designed as a metal ring.

It is important here that the inside diameter 18 of the support ring 10 extends beyond the outside diameter of the contact ring 6, so that the support ring 10 will be properly centered on the contact ring 6.

As a result of this external centering, it is simultaneously ensured that the resonator 1, which is glued in place in the area where the film ring 11 rests on it, is centered precisely in the measuring space 33 of the measurement chamber 36.

Figure 2:
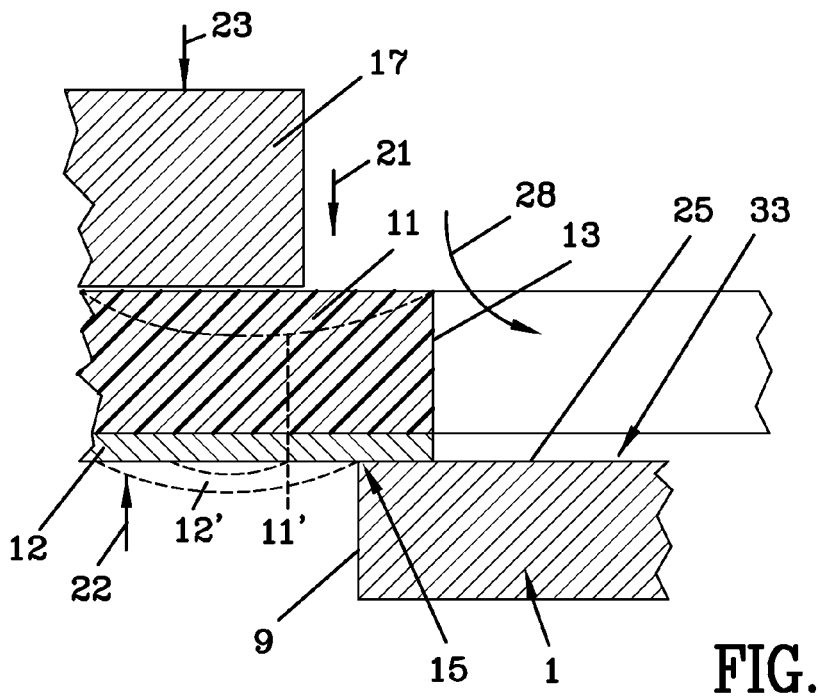
FIG. 2 shows an enlarged partial cross section through the measurement chamber of FIG. 1.

On an enlarged scale, FIG. 2 shows the special sealing action of the film ring 11 with respect to the resonator 1.

It can be seen here that, when an appropriate pressure is applied on the sealing ring by the measurement chamber in the direction of arrow 23, this applied pressure is transmitted downward in the direction of arrow 21 and does not act on the resonator 1. Instead, it is absorbed by the support ring. The amount of force which is applied to the resonator is defined precisely by the properties of the film and occurs only through the slight deformation of the film ring 11, shown in broken line. The adhesive surface 12 is also deformed into the position of the adhesive surface 12', shown in broken line. As a result, the inside circumference of the film ring wraps around the upper edge 15 of the outside circumference of the resonator 1 and results there in an especially effective and reliable seal.

It is therefore clear that, because of the thinness of the film ring 11 (shown with exaggerated thickness in FIG. 2), it is ensured that the liquid can be directed tangentially without loss onto the measurement surface 25, as indicated by the directional arrow 28.

The applied pressure or the sealing pressure is therefore transmitted downward in the direction of arrow 21 via the slightly deforming film ring 11 and introduced into the opposite, stationary contact surface or opposing surface, which is provided by the support ring 10 and which is illustrated symbolically only as the directional arrow 22 in FIG. 2.

This means that, regardless of how much force is applied, the force acting in the direction of arrow 21 and the corresponding opposing force acting in the direction of arrow 22 will always be present, and thus the resonator 1 remains reliably unaffected by that applied force.

The introduction or the transmission of a force in the direction of arrow 21 to the resonator occurs only by way of the slight deformation of the film and is therefore defined precisely by the properties of the film ring 11.

The seal is produced therefore not only in the area of the upper edge 15 but also in the overlapping area of the adhesive surface 12, that is, in the area where the inside diameter 13 of the film ring 11 wraps around the outside diameter of the resonator 1 and retains it. The seal is accomplished by the adhesive bond between the film and the quartz oscillator.

The invention is not limited, however, to this adhesive bonding. In another embodiment, a stronger film is used for mounting, which creates the seal simply by being pressed from above onto the resonator. It is also essential here that the inside diameter 16 of the sealing ring 17 does not act on the resonator 1—as is done disadvantageously in the state of the art—but rather rests on the outer section of the film ring 11.

The sealing surface between the sealing ring 17 and the film ring 11 is therefore created in the area of the sealing surface 19, and in the area of the support ring 10, it is created in the area of the contact surface 20. These two surfaces are always under the same load regardless of the sealing pressure, and this applied pressure is not as previously explained—introduced into the resonator 1.

The function of the measurement chamber 36 will now be explained in greater detail in conjunction with FIGS. 3-5.

In the outward-lying areas, channels 34, 35 are present, which proceed at an angle into the measuring space 33. The substance to be studied flows from the channel 34 in the direction of arrow 28 into the inflow space 32, which has the smallest possible volume and which is in liquid-flow connection with the measuring space 33 itself. After the substance has flowed tangentially over the measuring surface 25 of the resonator 1 in the direction of arrow 28, it flows onward in the direction of arrow 37 into the outflow space and from there into the channel 35 of the measuring chamber and is discharged from there.

It is important to note that the upper boundary of the measuring space 33 is formed by a vertically adjustable optical window 29, so that the nature and appearance of the measuring surface 25 can be checked at any time from above through the optical window 29.

The vertical adjustability is illustrated symbolically by the directional arrow 30 in FIG. 1.

The end surface 31 of the optical window 29 therefore forms a height-adjustable boundary of the gap between it and the measuring surface 25 of the resonator 1.

Of course, the invention is not limited to an angled introduction of substances into the measurement space 33 through slanting channels 34, 35. It is also possible for the channels 34, 35 in the measurement chamber 36 to be exactly parallel to the measuring surface 25 of the resonator 1.

The advantage of the thin film ring 11 used here is that tangential introduction is actually possible, because there are no interfering projections in the tangential direction extending across the measuring surface 25 of the resonator 1.

Figure 3:
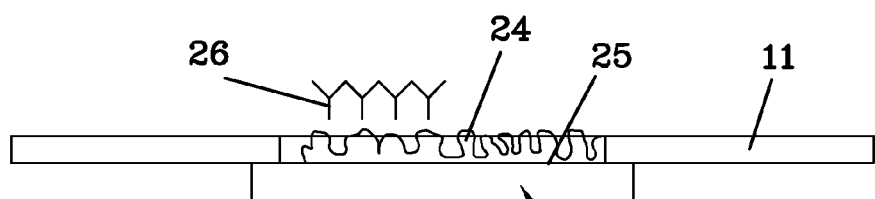
FIG. 3 shows a functional diagram with an illustration of material settling on the measurement surface.
Figure 4:
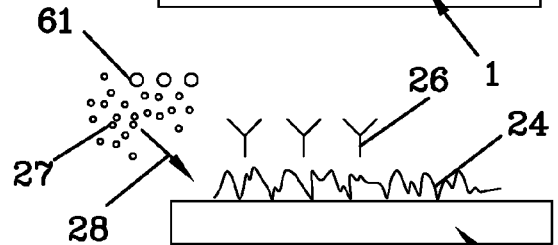
FIG. 4 shows a view similar to FIG. 3.
Figure 5:
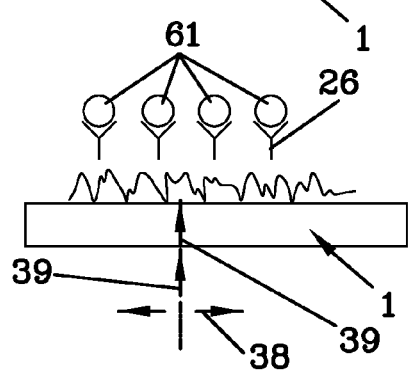
FIG. 5 shows a view similar to FIG. 4.

By way of example, the testing of the blood group of a sample of whole blood is explained in greater detail on the basis of FIGS. 3-5.

In preparation, the measuring surface 25 of the resonator 1 is first provided with a protein coating 24 (e.g., protein A), as shown in FIG. 3. This is a thin, schlieren-like layer.

Then IgG antibodies 26 are immobilized on the protein coating 24.

Now, as shown in FIG. 4, whole blood 27 is applied to the measuring surface 25, which has been produced and coated as explained above. As shown in FIG. 5, erythrocytes 61 are present in the whole blood.

The erythrocytes 61 bind to the IgG antibodies 26 by way of an immunoreaction.

Figure 6:
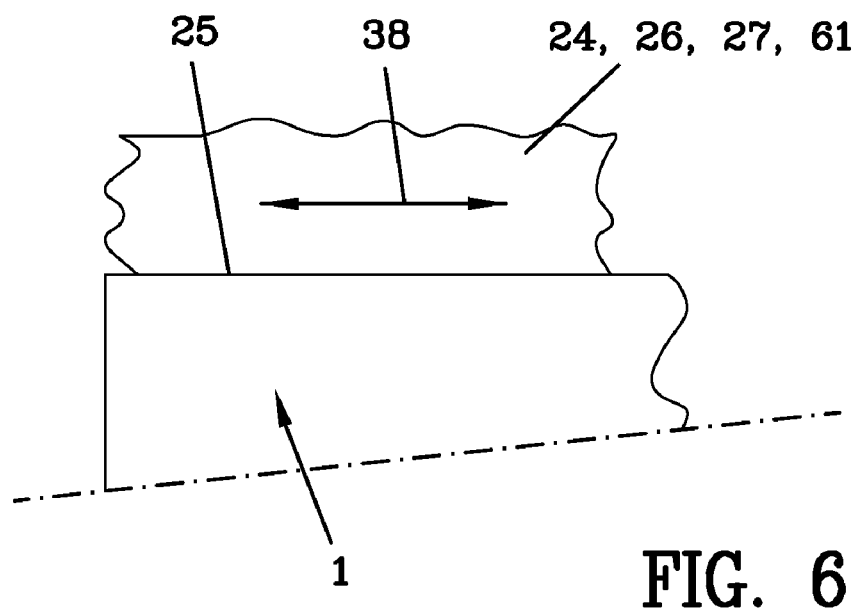
FIG. 6 shows a schematic diagram of the oscillation behavior of the substance to be studied on the measurement surface of the resonator.
Figure 11:
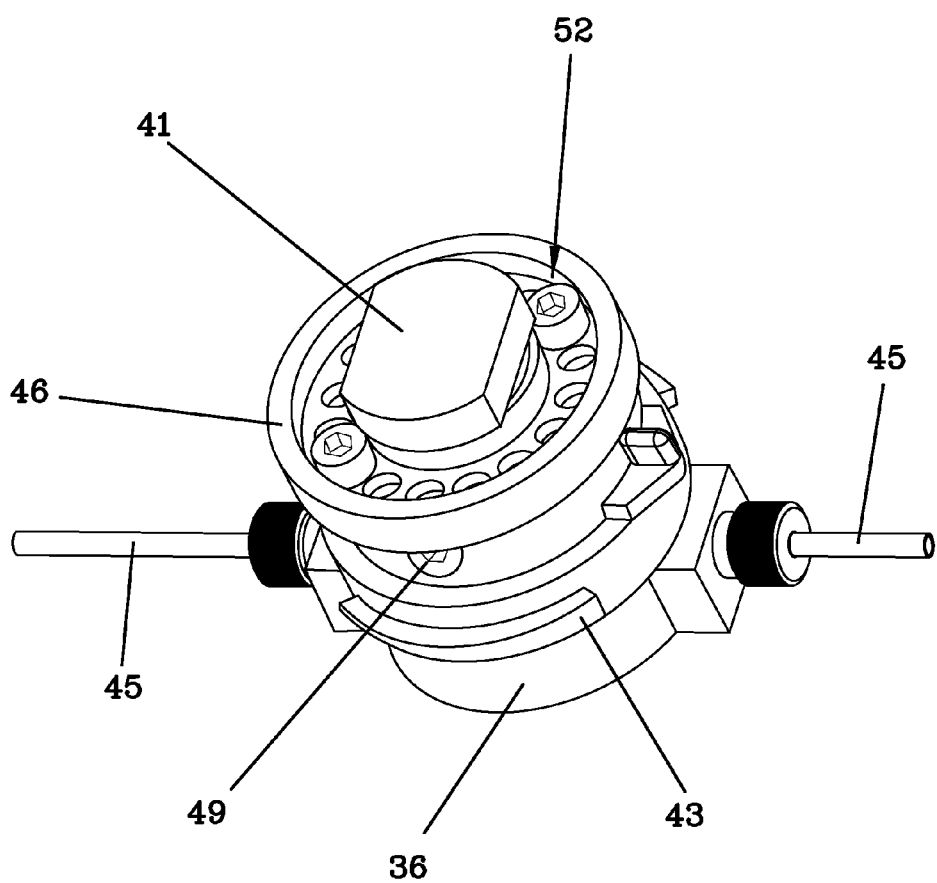
FIG. 11 shows a perspective side view of the measurement chamber.

During this time, the resonator 1 is being excited by an electrical AC voltage. A standing transverse wave forms in the interior of the resonator and propagates vertically upward (directional arrow 39) into the substance 24, 26, 27, 61. The two end surfaces 25 of the resonator therefore execute shear oscillation, which is illustrated schematically by the directional arrows 38. These relationships are shown in more detail in FIG. 6.

It can be seen that shear oscillations in the directions of arrow 38 are now being generated in the substance 24, 26, 27, 61 to be examined. These oscillations cause the substance to oscillate in concert.

The mechanical resonance frequency and/or the oscillation amplitude of the resonator 1 changes in correspondence with the mass loading and the damping of the measuring surface 25. The oscillator circuit supplying the resonator 1 causes the frequency of the electrical AC voltage to track the mechanical resonance frequency. The frequency change of the electrical AC voltage can be detected by a frequency counter and serves as a measure of the change in the amount of material present on the measuring surface 25 of the resonator 1.

By measuring the electrical impedance, it is possible to measure the damping caused by the accumulated layer.

FIGS. 7-11 show the design of a measurement chamber 36 in greater detail.

The measurement chamber 36 consists essentially of a metal or plastic housing 42, which defines a middle, central opening, into which the viewing plunger 41, consisting of a transparent plastic material (or of glass) is inserted in a height-adjustable manner.

The housing 42 is screwed tightly to a lower part (not shown) by means of any suitable type of quick-release screw fastener (e.g., a bayonet fastener). By way of example, the lower part in the form of a holder is indicated in FIG. 12 by the reference number 54.

Figure 12:
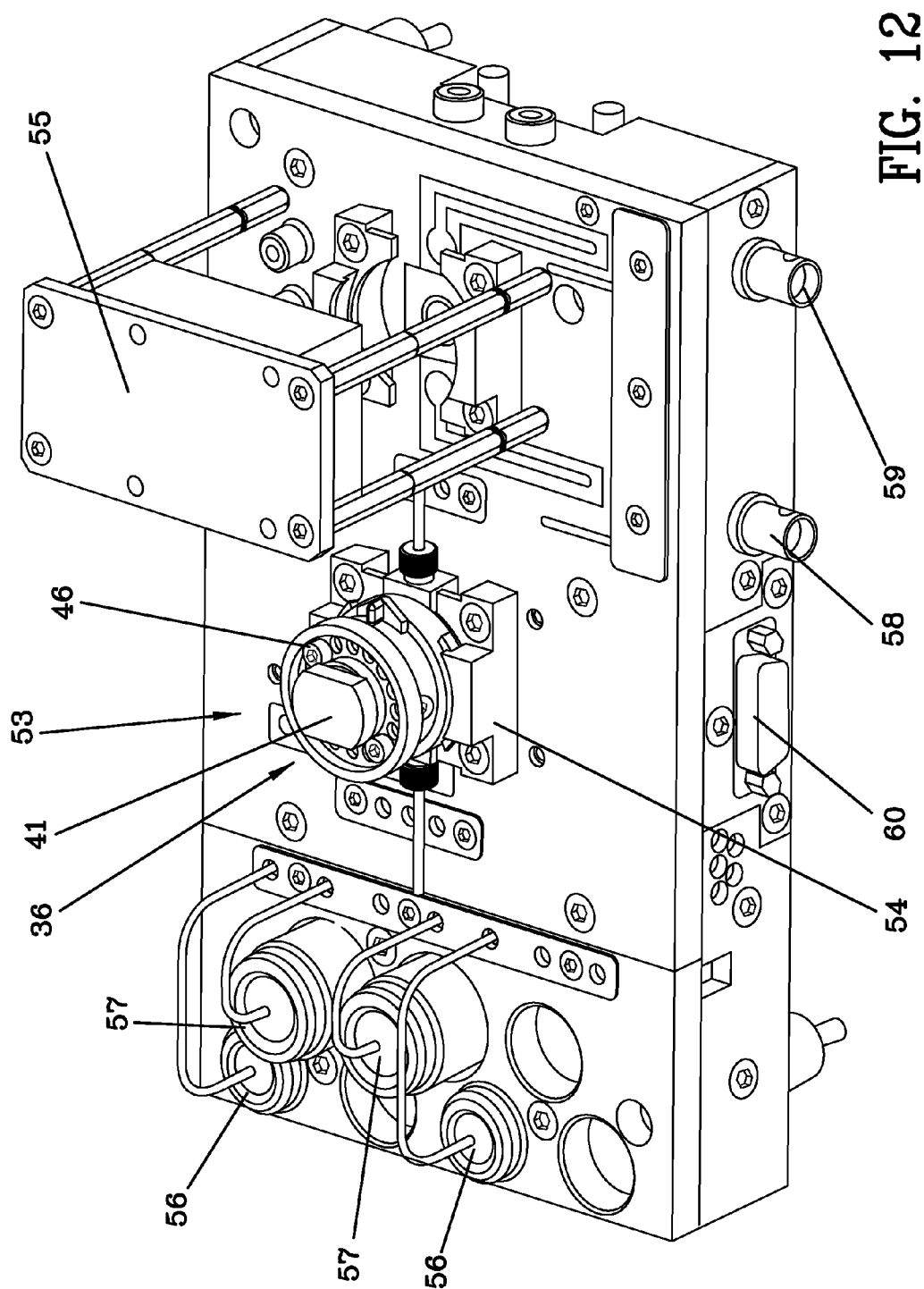
FIG. 12 shows a perspective view of a sensor unit with a mounted measurement chamber and a second receiving location for the arrangement of a second measurement chamber.

The bayonet flanges 43 therefore engage in their assigned receiving flanges on the holder 54 according to FIG. 12 and are held firmly in place there.

The previously mentioned sealing ring 17, which produces the seal between the housing and the measuring device, is located under the bottom end surface of the housing 42.

The housing is designed with essentially two stages, consisting of an upper part with a smaller diameter and a lower part 44 of larger diameter, the two parts being made out of a single piece of material.

The connecting tubes 45 for the introduction and discharge of the substance to be examined open into this lower part 44 of the housing.

To adjust the height of the viewing plunger 41, an adjusting wheel 46 is provided, which cooperates with a thread (not shown) on the housing 42.

By turning the adjusting wheel 46 in the directions of the rotational arrow 47, therefore, the viewing plunger 41 is moved vertically up and down. It is locked in place by a locking screw 49 in order to set the height of the measuring space 33.

The top end surface of the viewing plunger 41 forms a display window 48, through which it is possible to observe the surface of the resonator 1.

The adjusting wheel 46 has a series of display windows 48 arranged a certain distance apart around the circumference, so that the degree to which the adjusting wheel 46 is turned can be determined on the basis of an opposing measurement mark. The wheel is then fixed in place with the locking screw 52.

A locking screw 49 is also used to prevent the viewing plunger from rotating. This screw comes to rest with a clamping action against the outside circumference of the cylindrical viewing plunger 41.

FIG. 10 shows that the viewing plunger 41 is guided in the central opening 50 in a sealed manner by one or more O-ring seals 51.

FIG. 12 shows a complete sensor unit 53, in which two adjacent measurement chambers 36 are provided. The one measurement chamber 36 is fully equipped, but only a holder 55 for a CCD camera is arranged above the site of the other measurement chamber, the measurement chamber itself having been removed.

These two measurement chambers can be operated in series or in parallel.

For this purpose, a series of analyte vessels 56, to which buffer vessels 57 are assigned, are mounted in the sensor unit 53.

The desired test liquid is therefore taken from the analyte vessels 56 and displaced into the tubing, possibly in association with an upstream or downstream plug of buffer liquid from the buffer vessels 57.

Various electrical terminals are also provided on the sensor unit 53. The terminal 58 is the output of the oscillator circuit located in the sensor unit 53, and the terminal 59 is used to connect an impedance measuring device.

Various electrical signals and also the power supply arrive via the terminal 60 (which is designed as a multi-channel terminal).

In the interior of the sensor unit 53, Peltier elements are used to produce an absolutely temperature-stable environment, so that the entire sensor unit 53, together with the measurement chambers 36 present in it, is automatically maintained within a relatively narrow temperature range of, for example, ±0.06° C.

It is also possible to provide a thermostat-controlled water bath underneath the sensor unit 53, through which the analyte liquids can be conducted before they are injected into the measurement chambers 36.

LIST OF REFERENCE NUMBERS 1 resonator
2 contact surface
3 contact surface
4 contact surface
5 contact surface
6 contact ring
7 current leads
8 cavity
9 outside diameter (resonator 1)
10 support ring
11 film ring
11' deflected film ring
12 adhesive surface
12' deflected adhesive surface
13 inside diameter (film 11)
14 gap
15 upper edge (resonator 1)
16 inside portion
17 sealing ring
18 inside diameter (support ring 10)
19 sealing surface (sealing ring 17)
20 support surface (support ring 10)
21 directional arrow
22 directional arrow
23 directional arrow
24 protein coating
25 measuring surface
26 IgG antibodies
27 whole flood
28 directional arrow
29 optical window
30 directional arrow
31 end surface
32 inflow space
33 measuring space
34 channel
35 channel
36 measurement chamber
37 directional arrow
38 directional arrow
39 directional arrow
40 directional arrow
41 viewing plunger
42 housing
43 bayonet flange
44 lower part of housing
45 connecting tube
46 adjusting wheel
47 rotational direction
48 display window (fixation)
49 locking screw
50 opening
51 O-ring seal
52 locking screw
53 sensor unit
54 holder
55 holder for a CCD camera
56 analyte vessels
57 buffer vessels
58 terminal (oscillator)
59 terminal (impedance)
60 terminal
61 erythrocytes Those skilled in the art will readily recognize that the invention has been set forth by way of example only and that changes may be made thereto without departing from the spirit and scope of the appended claims.

The invention claimed is:

1. A measurement chamber in combination with a resonator (1), said resonator integrated into said measurement chamber for the analysis of a liquid in said resonator, said liquid includes materials, substances, and/or microorganisms, comprising:
    a housing;
    said resonator being disk-shaped;
    said disk-shaped resonator (1) in contact with said liquid;
    a contact ring, and, said resonator is supported by said contact ring;
    said disk-shaped resonator (1) includes an outside diameter and an outside circumference;
    said resonator includes a resonance frequency and/or damping, and, said resonance frequency and/or damping of said resonator dependent on said liquid containing said materials, substances, and/or microorganisms;
    an elastomeric film ring (11);
    a sealing ring (17), said sealing ring located between said housing and said elastomeric film ring (11);
    said elastomeric film ring engages said outside circumference of said resonator (1); and,
    said elastomeric film ring (11) seals said outside circumference of said resonator.

2. A measurement chamber and a resonator according to claim 1, wherein said resonator (1) includes two, flush mounted electrical contact surfaces (2, 3).

3. A measurement chamber and a resonator according to claim 1, further comprising:
    said contact ring (6) having electrical contact surfaces (4, 5) wherein said electrical contact surfaces (2, 3) rest with a precisely defined contact pressure on said contact surfaces (4, 5) of said contact ring (6); said contact surfaces (4, 5) arranged oppositely from said contact surfaces (2, 2); respectively; and, said contact ring made of electrically insulating material.

4. A measurement chamber and a resonator according to claim 3, wherein each of said contact surfaces (4, 5) is connected by a current lead (7) to an electrical circuit which monitors the mechanical oscillation of the resonator (1).

5. A measurement chamber and a resonator according to claim 4, wherein said elastomeric film ring (11) includes an inside diameter (13) which extends over and engages said outside circumference of said resonator (1), said resonator (1) is mounted and sealed without any mechanical stress.

6. A measurement chamber and a resonator according to claim 5, wherein said elastomeric film ring (11) is held between surfaces (19, 20) of said sealing ring (17) and said support ring (10).

7. A measurement chamber and a resonator according to claim 6, further comprising:
said sealing ring includes a lower surface;
said support ring includes an upper surface;
and wherein said lower surface of said sealing ring (17) and said upper surface of said support ring (10) seal against said elastomeric film ring (11) and said upper surface of said sealing ring (17) seals against said housing, said sealing ring (17) spaced radially outward a certain distance away from said outside circumference of said resonator (1).

8. A measurement chamber and a resonator according to claim 7, further comprising:
said housing includes a surface;
said housing engages said sealing ring creating a seal therebetween;
a support ring, said support ring made of dimensionally stable material;
said sealing ring spaced apart from said resonator;
said support ring and said housing supporting said sealing ring;
and, said resonator (1) is free-floating.

9. A measurement chamber and a resonator according to claim 8, further comprising:
a measuring space;
said support ring includes an inside diameter (18) and wherein said contact ring (6) includes an outside diameter;
said support ring includes an inside diameter (18);
said contact ring includes an outside diameter;
said inside diameter (18) of said support ring (10) extends beyond said outside diameter of the contact ring (6);
said inside diameter of said support ring (10) is centered with respect to said sealing ring (17);
and, said resonator (1) is centered precisely in the middle of the measuring space (33) by said elastomeric film ring (11).

10. A measurement chamber and a resonator according to claim 9, wherein said elastomeric ring (11) which holds said resonator (1) comprises an adhesive layer (12).

11. A measurement chamber and a resonator according to claim 10, further comprising:
said elastomeric film ring includes an outer circumference;
said resonator includes an upper edge;
wherein a pressure applied onto the upper sealing ring (17) is transmitted downward onto said elastomeric film ring (11) deforming (11') said elastomeric film ring, and deforming (12') said adhesive surface (12), and, said outer circumference of said elastomeric film ring (11) engaging said upper edge (15) of said outside circumference of said resonator (1).

12. A measurement chamber and a resonator according to claim 11, wherein force transmitted downward onto said elastomeric film ring (11) generates a counterforce upward preventing the introduction of force to said resonator (1).

13. A measurement chamber and a resonator according to claim 12, further comprising:
said resonator includes a measuring surface (25); and,
wherein said elastomeric ring (11) ensures loss-free tangential flow onto said measuring surface (25).

14. A measurement chamber and a resonator according to claim 13, wherein said elastomeric ring (11) is attached directly to the surface of said resonator (1) and said measurement chamber (36) including said elastomeric ring (11) is completely flat.

15. A measurement chamber and a resonator according to claim 14, wherein said channel (35) of said resonator (1) is completely sealed.

16. A measurement chamber and a resonator according to claim 15, wherein the mounting of resonator (1) forms a path for a tangential flow introduction.

17. A measurement chamber and a resonator according to claim 16, wherein said resonator (1) comprises a quartz oscillator surface, where, said resonator (1) includes a surface and, said measurement chamber (36) comprises a vertically adjustable optical window (29) which forms an upper boundary of the measuring space (33) and allows the monitoring of said measuring surface (25).

18. A measurement chamber and a resonator according to claim 17, further comprising an inflow space (32) and channels (34, 35) in communication with said measuring space (33).

19. A measurement chamber and a resonator according to claim 18, wherein tangential flow over said measuring surface (25) of said resonator (1) is discharged from the outflow space into channel (35) of said measurement chamber.

20. A measurement chamber and a resonator according to claim 19, wherein said optical window includes an end surface and wherein said end surface (31) of said optical window (29) forms a height-adjustable gap between said optical window and said measuring surface (25) of said resonator (1).

21. A measurement chamber and a resonator according to claim 20, wherein said channels (34, 35) in the measurement chamber (36) extend parallel to the measuring surface (25) of the resonator (1).

22. A measurement chamber and a resonator according to claim 21, wherein:
said liquid includes whole blood (27);
said whole blood (27) includes a coating (24) and antibodies (26);
said measuring surface (25) of said resonator (1) is provided with said coating (24) such as a protein A, on which said antibodies such as IgG antibodies (26) are immobilized.

23. A measurement chamber and a resonator according to claim 22, wherein: said whole blood (27) includes erythrocytes (61), said erythrocytes (61) in whole blood (28) attach themselves to said IgG antibodies (26) while said resonator (1) is excited by an AC voltage; a transverse wave with a vertical deflection direction (39) is formed and propagates in the direction of arrow 38; and, said whole blood is excited to perform the same oscillations.

24. A measurement chamber and a resonator according to claim 23, wherein the mechanical resonance frequency of said resonator (1) changes in correspondence with mass loading of measuring surface (25) and is tracked by an oscillator circuit supplying said resonator (1) where the change in frequency which occurs serves as a measure of the change in the mass loading of the measuring surface (25) of the resonator (1).

25. A measurement chamber and a resonator according to claim 24, wherein the damping of said resonator oscillations caused by said whole blood is measured as electrical impedance.

26. A measurement chamber and a resonator according to claim 25, further comprising:
a two-stage housing (42);
said two-stage housing includes a middle, center opening;
a vertically adjustable viewing plunger (41) resides in said middle, center opening of said two-stage housing.

27. A measurement chamber and a resonator according to claim 26, further comprising:
a holder (54);
said holder (54) includes a lower part (44) and receiving flanges, said lower part includes bayonet flanges (43);
a quick-release bayonet fastener;
said two-stage housing (42) is arranged on said holder (54) by means of said quick-release bayonet fastener;
said lower part (44) of said housing has bayonet flanges (43) which engage said receiving flanges of said holder (54).

28. A measurement chamber and a resonator according to claim 27, further comprising:
connecting tubes (45);
said connecting tubes (45) communicate with said lower part (44) of said housing.

29. A measurement chamber and a resonator according to claim 28, further comprising:
said housing includes threads;
a locking screw (49);
an adjusting wheel (46);
said measuring space (33) has a height;
wherein said height of said measuring space (33) can be adjusted by means of said viewing plunger (41);
wherein said adjusting wheel (46) cooperates with said threads on said housing;
and, wherein said viewing plunger (41) moves up and down, and the position of said viewing plunger then being fixed in place by means of said locking screw (49).

30. A measurement chamber and a resonator according to claim 29, wherein said adjusting wheel (46) comprises a series of display windows (48) arranged in a ring around the circumference thereof.

31. A measurement chamber and a resonator according to claim 29, wherein a sensor unit (53) comprises several adjacent measurement chambers (36).

32. A measurement chamber and a resonator according to claim 31, wherein said sensor unit (53) comprises electrical terminals and an oscillator circuit, and wherein said oscillator circuit further comprises an output terminals (58, 59, 60).

33. A measurement chamber and a resonator according to claim 32, wherein said sensor unit (53) has Peltier elements which provide an absolutely temperature-stable environment, and wherein said sensor unit (53) forms an automatic temperature control system which remains stable within a relatively narrow range of, for example, ±0.06° C.

34. A measurement chamber and a resonator according to claim 33, wherein said sensor unit includes a thermostat-controlled water bath.

35. A measurement chamber in combination with a resonator (1) as claimed in claim 1, further comprising:
a support ring (10);
said elastomeric film ring includes adhesive thereon;
said elastomeric film ring resides between said sealing ring and said support ring; and,
said adhesive engages said outside circumference of said resonator and said support ring securing said elastomeric film ring to said resonator and said support ring.

36. A measurement chamber in combination with a resonator (1) as claimed in claim 1, further comprising:
said resonator includes a measuring surface;
an optical window resides within said housing;
said optical window includes an end surface; and,
a measuring space formed between said end surface of said optical window and said measuring surface of said resonator.

37. A measurement device, comprising:
a resonator, said resonator being disk-shaped, and, said resonator includes an outer radial portion;
a contact ring, and, said resonator is supported by said contact ring;
an elastomeric film ring, said elastomeric film ring includes an inner radial portion and an outer radial portion, and, said inner radial portion of said elastomeric film ring affixed to said outer radial portion of said resonator;
a support; a seal; a housing; and,
said elastomeric film ring affixed to said support, said seal interposed between said housing and said elastomeric film ring.

38. A measurement device as claimed in claim 37, further comprising:
said resonator includes a measuring surface;
an optical window resides within said housing;
said optical window includes an end surface; and,
a measuring space formed between said end surface of said optical window and said measuring surface of said resonator.

39. A measurement chamber in combination with a resonator (1), said resonator integrated into said measurement chamber for the analysis of a liquid in said resonator, said liquid includes materials, substances, and/or microorganisms, comprising:
a housing;
said resonator being disk-shaped;
said disk-shaped resonator (1) in contact with said liquid;
said disk-shaped resonator (1) includes an outer radial portion;
a contact ring, and, said resonator is supported by said contact ring;
said resonator includes a resonance frequency and/or damping, and, said resonance frequency and/or damping of said resonator dependent on said liquid containing said materials, substances, and/or microorganisms;
an elastomeric film ring (11);
a sealing ring (17), said sealing ring located between said housing and said elastomeric film ring (11);
said elastomeric film ring engages said outer radial portion of said resonator (1); and,
said elastomeric film ring (11) engages and seals said outer radial portion of said resonator.

40. A measurement chamber in combination with a resonator (1) as claimed in claim 39, further comprising:
a support ring (10);
said elastomeric film ring includes adhesive thereon;
said elastomeric film ring resides between said sealing ring and said support ring; and,
said adhesive engages said outer radial portion of said resonator and said support ring securing said elastomeric film ring to said resonator and said support ring.

41. A measurement chamber in combination with a resonator (1) as claimed in claim 39, further comprising:
said resonator includes a measuring surface;
an optical window resides within said housing;
said optical window includes an end surface; and,
a measuring space formed between said end surface of said optical window and said measuring surface of said resonator.

* * * * *